(12) United States Patent
Capuzzi et al.

(10) Patent No.: US 11,123,274 B2
(45) Date of Patent: Sep. 21, 2021

(54) COSMETIC COMPOSITIONS CONTAINING DIGLYCEROL TETRAPELARGONATE

(71) Applicant: Novamont S.p.A., Novara (IT)

(72) Inventors: Luigi Capuzzi, Novara (IT); Francesca DiGioia, Barengo (IT); Vanessa Bramati, Lainate (IT); Federica Carlomagno, Saronno (IT); Alessandra Cominetti, Agnadello (IT)

(73) Assignee: NOVAMONT S.P.A., Novara (IT)

( * ) Notice: Subject to any disclaimer, the term of this patent is extended or adjusted under 35 U.S.C. 154(b) by 0 days.

(21) Appl. No.: 16/099,036

(22) PCT Filed: May 4, 2017

(86) PCT No.: PCT/EP2017/060678
§ 371 (c)(1),
(2) Date: Nov. 5, 2018

(87) PCT Pub. No.: WO2017/191268
PCT Pub. Date: Nov. 9, 2017

(65) Prior Publication Data
US 2019/0192401 A1  Jun. 27, 2019

(30) Foreign Application Priority Data

May 6, 2016  (IT) .................. 102016000046996

(51) Int. Cl.
| | | |
|---|---|---|
| *A61K 8/37* | (2006.01) | |
| *A61Q 19/00* | (2006.01) | |
| *A61Q 5/00* | (2006.01) | |
| *A61Q 1/10* | (2006.01) | |
| *A61Q 17/04* | (2006.01) | |
| *A61Q 19/10* | (2006.01) | |
| *A61Q 1/06* | (2006.01) | |
| *A61K 8/92* | (2006.01) | |

(52) U.S. Cl.
CPC ............... *A61K 8/375* (2013.01); *A61Q 1/06* (2013.01); *A61Q 1/10* (2013.01); *A61Q 5/00* (2013.01); *A61Q 17/04* (2013.01); *A61Q 19/00* (2013.01); *A61Q 19/10* (2013.01); *A61K 8/92* (2013.01); *A61K 2800/10* (2013.01)

(58) Field of Classification Search
CPC ...... A61K 8/375; A61K 2800/10; A61K 8/92; A61Q 1/06; A61Q 17/04; A61Q 19/00; A61Q 19/10; A61Q 1/10; A61Q 5/00
See application file for complete search history.

(56) References Cited

U.S. PATENT DOCUMENTS

2004/0175338 A1* 9/2004 Filippi .................. A61K 8/37
424/64

FOREIGN PATENT DOCUMENTS

| DE | 20 2008 006004 U1 | 7/2008 | |
|---|---|---|---|
| EP | 3 006 499 A1 | 4/2016 | |
| FR | 2 925300 A1 | 6/2009 | |
| JP | WO 2014/192812 | * 12/2014 | ............. C08L 23/00 |
| WO | WO 94/07460 A1 | 4/1994 | |

* cited by examiner

*Primary Examiner* — Jeffrey T. Palenik
(74) *Attorney, Agent, or Firm* — Polsinelli PC

(57) ABSTRACT

The invention concerns cosmetic compositions comprising diglycerol tetrapelargonate, or a mixture of diglycerol tetrapelargonate with one or more esters selected from neopentylglycol dipelargonate, glycerol tripelargonate, pentaerythritol tetrapelargonate, and their use for the care of the skin and hair, and in make-up and in hygiene products.

21 Claims, No Drawings

COSMETIC COMPOSITIONS CONTAINING DIGLYCEROL TETRAPELARGONATE

CROSS REFERENCE TO RELATED APPLICATIONS

This application is a National Phase filing under 35 U.S.C. § 371 of PCT/EP2017/060678 filed on May 4, 2017; which in turn claims priority to Application No. 10/2016000046996 filed in Italy on May 6, 2016. The entire contents of each application are hereby incorporated by reference.

This invention relates to the use of diglycerol tetrapelargonate in cosmetic compositions and cosmetic compositions containing it.

In the cosmetics industry increasing attention is being paid to the identification of new low-environmental-impact ingredients of natural and renewable origin which at the same time have optimum functional and sensory properties.

The cosmetic compositions are used in the care of the skin and hair, in make-up and in hygiene products and commonly have a lipophilic component which depending upon the substance contributes to ensuring optimum detergency, hydration and softening, contributes to lubrication and the applicability of the product, the dispersion of solar filters, colouring agents, active ingredients and additives and/or acts as a binder, encouraging adhesion between the various ingredients, for example in cosmetic compositions such as eye shadows and compact powders.

Some esters of polyglycerols such as diglycerol, of plant origin, are for example used in products for care of the person as emulsifying agents, thanks to their action as non-ionic surfactants.

It has now in particular been observed that the tetra ester of diglycerol with pelargonic acid, which can also be obtained from renewable sources, has special lubricating capacities and imparts a soft and smooth appearance to the skin, unlike other diglycerol tetraesters as diglycerol tetraoleate which are mainly used for their emulsifying properties. Diglycerol tetrapelargonate is also capable of maintaining hydration of the skin thanks to its ability to form a barrier which slows the loss of water from the skin. It also has a binding action on powders and has an optimum capacity for dispersing solar filters, pigments, active ingredients and other additives.

Diglycerol tetrapelargonate is therefore suitable for use as an ingredient of the lipophilic component in compositions which are physiologically acceptable for cosmetic use, i.e. for the preparation of products intended for application to the outer surface of the human body (epidermis, lips and cutaneous annexes) in order exclusively or mainly to clean them, perfume them, modify their appearance, protect them, maintain them in a good condition or correct body odours.

By suitably adjusting the quantity of ester in a formulation it is possible to obtain anhydrous compositions and aqueous compositions having excellent properties suitable for an extensive range of applications.

The object of this invention therefore relates to the use of diglycerol tetrapelargonate for the preparation of cosmetic compositions and cosmetic compositions containing it.

According to an advantageous aspect of the invention, the diglycerol tetrapelargonate ester is prepared from pelargonic acid from renewable sources, obtained for example by processes of the oxidative cleavage of vegetable oils, fatty acids and their derivatives, which may or may not be modified.

Preferred examples of renewable sources of pelargonic acid are vegetable oils from sunflowers, brassicaceae or thistles (such as *Cynara cardunculus* and *Silybum marianum*). Particularly preferred sources of pelargonic acid are represented by vegetable oils having a high oleic or erucic acid content.

The said pelargonic acid is preferably obtained by oxidative cleavage processes in which inorganic and organic peroxides, peracids, nitric acid, permanganates, periodates, $O_2$, $O_3$ or their gaseous mixtures are used as oxidising agents.

Oxidative cleavage processes in which peroxides such as hydrogen peroxide and $O_2$ or mixtures containing $O_2$ are used as oxidising agents are preferred. Specific examples are the oxidative cleavage processes described in applications WO 94/10122, WO 07/039481, WO 2008/138892, WO 2011/080296, WO 2011/080297 or WO 2013/079849.

The abovementioned ester is preferably prepared through an esterification reaction starting from pelargonic acid of high purity, preferably in excess of 95%, more preferably in excess of 98%, and diglycerols of purity preferably in excess of 90%, having a glycerol content of preferably less than 10% and less than 15% of higher polyglycerols. Preparation through esterification is advantageously performed in the absence of catalyst.

The said esterification is advantageously carried out in the presence of a molar excess of pelargonic acid with respect to the moles of diglycerol, preferably of or greater than 30% and less than 70%, operating at temperatures typically between 180 and 240° C., preferably 200-210° C. The water forming during the esterification reaction is advantageously removed from the reaction environment, for example by applying a gradual reduction in pressure; at the end of the reaction the excess acid is removed, preferably by evaporation. The ester so obtained can advantageously undergo purification treatments according to processes known to those skilled in the art, for example using activated carbons and decolouring earths with a view to removing any colouration, odour and residual acidity. Examples of decolouring earths which may be used, including in combination with activated carbons, are Grade F-118FF, Grade F76 (marketed by BASF), Minclear N100, Minclear E100 and Pansil 2 (marketed by Tolsa).

In comparison with esters obtained by the common esterification procedures catalysed by metals, for example tin, the esters obtained by operating in accordance with the procedure described above do not contain metal residues which might influence their organoleptic properties (e.g. colour, odour) and their stability, and the toxicological properties of the finished cosmetic products. They therefore have the particular advantage of a lesser inorganic material content and require simplified preliminary treatments for use in the cosmetic environment.

The object of the invention also relates to mixtures of diglycerol tetrapelargonate with one or more esters of pelargonic acid selected from neopentylglycol dipelargonate, glycerol tripelargonate and pentaerythritol tetrapelargonate and cosmetic compositions comprising the said mixtures.

The said compositions may be prepared for example by adding the said esters of pelargonic acid to the other ingredients separately (one at a time) or simultaneously, after they have been previously mixed.

The cosmetic compositions according to the invention may contain from 0.1% to 99% by weight of diglycerol tetrapelargonate with respect to the total weight of the composition. They may be in the form of lipophilic cosmetic compositions (i) or in the form of aqueous cosmetic compositions (ii), in each case having a characteristic optimum content of diglycerol tetrapelargonate.

Lipophilic Cosmetic Compositions (i)

Diglycerol tetrapelargonate is particularly suitable as an ingredient for the oily component in cosmetic compositions intended for the preparation of oils, butters, concealers, lipsticks and sun creams, in which, as a result of its special combination of functional and sensory properties it may surprisingly constitute the only ingredient of the oily component.

It is also suitable as a binding agent in compositions in the form of compact powders such as eye shadow, blushers, powders and foundation creams.

A preferred aspect of the invention therefore relates to "lipophilic" cosmetic compositions comprising diglycerol tetrapelargonate, i.e. cosmetic compositions consisting mainly of lipophilic ingredients such as oils and fats, comprising diglycerol tetrapelargonate.

The compositions of a lipophilic nature according to the invention comprise an oily component which in turn comprises or advantageously consists of diglycerol tetrapelargonate according to the invention. The said lipophilic compositions advantageously comprise up to 99% by weight, preferably up to 95%, of the said ester with respect to the weight of the cosmetic composition, optionally in the form of a binary, ternary or quaternary mixture with the above-mentioned esters of pelargonic acid.

In addition to the ester or mixture of esters mentioned above, the said oily component may comprise other oils of vegetable, animal, mineral and/or synthetic origin, preferably selected from esters, amides, ethers, alcohols and hydrocarbons of natural and/or synthetic origin, silicone oils or mixtures thereof.

Possible examples of esters of natural origin are triglycerides of saturated or unsaturated fatty acids, such as for example triglycerides of C8 and C10 acids, or their mixtures such as for example those present in vegetable oils. Suitable vegetable oils are for example olive oil, sunflower oil, maize oil, soya oil, castor oil, apricot oil, avocado oil, almond oil, macadamia oil, jojoba oil or karite oil.

Esters of synthetic origin are for example esters of linear and branched carboxylic acids with monoalcohols, such as isononyl isononanoate, isopropyl myristate, 2-ethy hexyl palmitate, isodecyl neopentanoate, isostearyl neopentanoate, 2-octyldodecyl stearate, 2-octyldodecyl erucate or isostearyl isostearate, diisostearyl maleate, C12-15 alkyl benzoate; esters of C7-C10 chain fatty acids with fatty alcohols; hydroxylated esters, such as isostearyl lactate, octyl hydroxystearate, octyldodecyl hydroxystearate; esters of polyols, such as propylene glycol dioctanoate, neopentyl glycol diheptanoate or diethylene glycol diisononanoate and pentaerythrityl tetraisostearate.

One example of an ether is dicaprilyl ether. One example of an amide is dibutyl lauroyl glutamide.

Other examples of oils include fatty alcohols such as octyldodecanol, hexyldodecanol, isostearyl alcohol.

Hydrocarbon oils of natural origin are for example terpene hydrocarbons such as squalene and squalane; hydrocarbon oils of mineral or synthetic origin are for example liquid paraffin and its derivatives such as isoparaffins (e.g. isododecane, isohexadecane, polydecene hydrogenate) and cycloparaffins.

The silicone oils are synthetic compounds based on silicon; they may be volatile or non-volatile, linear or cyclic. Examples of silicone oils are polysiloxanes and their derivatives comprising for example alkyl, alkoxyl or phenyl groups; silicone oils typically used include the polydimethylsiloxanes (Dimethicone), Amodimethicone, Cyclomethicones such as Cyclopentasiloxane and Cyclohexasiloxane, Amino Bispropyl Dimethicone, Aminopropyl Dimethicone, Amodimethicone hydroxystearate, Behenoxy-Dimethicone, C30-45 Alkyl Dimethicone, C24-28 Alkyl Dimethicone, C30-45 Alkyl Methicone, Cetearyl Methicone, Cetyl Dimethicone, Dimethoxysilyl Ethylenediaminopropyl Dimethicone, Hexyl Methicone, Hydroxypropyldimethicone, Stearamidopropyl Dimethicone, Stearoxy Dimethicone, Stearyl Methicone, Stearyl Dimethicone and Vinyl Dimethicone.

Advantageously the cosmetic compositions according to the invention comprise one or more components deriving from the insaponifiable fraction of vegetable oils (for example, carotenoids, xanthophylls, tocopherols, phytosterols, aliphatic and terpene alcohols). Vitamins and active ingredients of a lipophilic nature may also be present dissolved in the oily component.

The lipophilic compositions according to the invention may advantageously also comprise one or more waxes in quantities of typically between 0.1 and 35% by weight with respect to the total weight of the composition. Those skilled in the art will be readily able to adjust the quantities and types of waxes which are to be used on the basis of their desired effect in the cosmetic composition.

By the term "wax" is meant a lipophilic component which is solid at ambient temperature (25° C.) and atmospheric pressure; the said component imparts viscosity, plasticity and strength to the cosmetic compositions containing it, which are therefore suitable for preparation in solid form, for example as sticks.

Waxes which are suitable for use in the cosmetic compositions according to the invention are all the waxes typically used in cosmetic compositions, which may be of natural and/or synthetic origin. Examples of natural waxes are beeswax or cera alba, carnauba wax, candelilla wax, Japan wax, rice wax, waxes deriving from hydrogenated oils, such as jojoba oil or sunflower or coconut oils, esters of long chain fatty acids with long chain monoalcohols or their glycerides, such as cetyl palmitate, cetyl stearate, palmitic and stearic triglycerides.

Examples of mineral or synthetic waxes are lignite wax, microcrystalline wax, paraffin, ozokerite, ceresin, synthetic beeswax, lanolin and their ethers with polypropylene glycols, polyethylene waxes, esters of fatty acids having a melting point over 25° C., polyamides, and cetyl esters. Silicone waxes such as alkyl or alkoxy-dimethicones or poly(di)methylsiloxanes having a high molecular weight may also be used.

Advantageously the cosmetic compositions according to the invention comprise one or more components deriving from the insaponifiable fraction of vegetable oils (for example carotenoids, xanthophylls, tocopherols, phytosterols, aliphatic and terpene alcohols). Vitamins and active ingredients of a lipophilic nature may also be present dissolved in the oily component.

According to a particularly preferred embodiment the invention relates to cosmetic compositions in lipophilic form comprising, with respect to the weight of the cosmetic composition:
  a) from 50 to 99% by weight, preferably from 55 to 95%, more preferably from 40 to 80%, of an oily component comprising diglycerol tetrapelargonate, optionally in a mixture with at least one ester selected from neopentyl glycol dipelargonate, glycerol tripelargonate and pentaerythritol tetrapelargonate;
  b) from 1 to 35% by weight, preferably from 5 to 30%, more preferably from 7 to 20%, of one or more waxes;

c) from 0 to 30% by weight, preferably from 0.1 to 20% by weight, more preferably from 0.1 to 15%, of one or more colouring agents;
d) from 0 to 3%, preferably from 0.05 to 2% by weight of vitamins and/or antioxidants;
e) from 0 to 2% by weight, preferably from 0.01 to 1%, of one or more preservatives.

The said composition is particularly suitable for the preparation of lipsticks, butters and balms for the lips, concealers, foundation creams and cast and stick eye shadows. The compositions comprising tetra ester of diglycerol with pelargonic acid according to this aspect of the invention have shown higher softness and flowability when compared to compositions comprising different tetra esters such as pentaerythritol tetrapelargonate or diglycerol tetraoleate.

The compositions according to the invention may advantageously also comprise one or more sun filters in quantities of preferably between 0.05% and 35% by weight, preferably between 0.1 and 30%, with respect to the weight of the cosmetic composition.

Sun filters have the function of protecting skin and/or hair from UVA/UVB radiation. These include for example filters or physical screens with reflecting properties such as for example zinc oxide and titanium dioxide, either in the form of nanomaterials or having particles of larger size, silica, kaolin, iron and/or magnesium oxides, and chemical filters, typically organic molecules capable of absorbing and converting the energy of ultraviolet radiation such as cinnamates, benzoimidazoles, benzophenones, benzylidene camphorate, PABA and its derivatives, salicylates, anthranylates, dibenzoyl methanes, octocrylene, triazines such as octyltriazone, bis-ethylhexyloxyphenol methoxyphenyl triazine and diethyl hexyl butamido triazone, natural antioxidants such as vitamin C and vitamin E or synthetic vitamins, such as Tinogard TT, or their combinations.

Physical and chemical filters may be of natural origin (such as for example gamma orizanol) or synthetic, and be used alone or more advantageously in combination.

Specific examples of sun filters suitable for use in the compositions according to the invention are octyl-methoxycinnamate, 2-ethyl-hexyl-4-dimethylaminobenzoate, butyl-methoxy-dibenzoylmethane, octyl triazone, diethyl hexylbutamido triazone, ethyl hexyl salicylate, zinc oxide, titanium dioxide, or their combinations.

According to a particularly preferred embodiment the invention relates to a lipophilic cosmetic composition comprising, with respect to the weight of the cosmetic composition:
a) from 50 to 99% by weight, preferably from 50 to 90%, of an oily component comprising diglycerol tetrapelargonate, optionally in a mixture with at least one ester selected from neopentyl glycol dipelargonate, glycerol tripelargonate and pentaerythritol tetrapelargonate and their mixtures;
b) from 0.05 to 35% by weight, preferably from 0.1 to 30%, of one or more sun filters;
c) from 0 to 30% by weight, preferably from 5 to 30%, more preferably from 7 to 20%, of one or more waxes;
d) from 0 to 30% by weight, preferably from 0.1 to 3%, of one or more colouring agents;
e) from 0 to 2% by weight, preferably from 0.01 to 1%, of one or more preservatives.

The said composition is particularly suitable for the preparation of sun protection products, for example sun protection sticks, oils and butters.

The compositions according to the invention may advantageously also comprise one or more polyolefins, acrylic derivatives, polyamide and/or polyester oligomers, for example selected from polybutylene or polyisobutylene.

Lipophilic compositions comprising from 15 to 85% by weight of the aforesaid oligomers, and from 5 to 65% by weight, preferably between 10 and 35% by weight, of oily component with respect to the total weight of the cosmetic composition are preferred. The said compositions also advantageously comprise suspended powders, colouring agents and antioxidants. Cosmetic compositions of this type are particularly suitable for the preparation of cosmetics such as lip gloss.

By "oligomers" are typically meant oligomers and polymers having a molecular weight of below 1000 g/mole, which are liquid at ambient temperature (25° C.) and atmospheric pressure, which are responsible for providing brightness and tack to the cosmetic composition.

Suitable oligomers are selected from the group comprising polybutylenes, polyisobutylenes and hydrogenated polyisobutylenes, polydecenes and hydrogenated polydecenes, polyethylene, polyamides, polyesters. Preferred oligomers are selected from polybutylene, polyisobutylene and/or polyamides.

According to a particularly preferred embodiment the invention relates to a lipophilic cosmetic composition comprising, with respect to the weight of the cosmetic composition:
a) from 15 to 85% by weight, preferably from 20 to 80%, of one or more oligomers;
b) from 5 to 65% by weight, preferably from 10 to 35%, of an oily component comprising diglycerol tetrapelargonate, optionally in a mixture with at least one ester selected from neopentyl glycol dipelargonate, glycerol tripelargonate and pentaerythritol tetrapelargonate and their mixtures;
c) from 0 to 15% by weight, preferably from 2 to 5%, of one or more flow modifiers (rheological modifiers) having suspension powers;
d) from 0 to 20% by weight, preferably from 0.1 to 15%, of one or more colouring agents;
e) from 0 to 5% by weight, preferably from 0.1 to 3%, of one or more waxes;
f) from 0 to 3% by weight, preferably from 0.05 to 2%, of vitamins and/or antioxidants;
g) from 0 to 2% by weight, preferably from 0.01 to 1%, of one or more preservatives.

The said composition is particularly suitable for the preparation of lip glosses.

By "rheological modifiers" are meant gelling agents, viscosity-imparting agents, dispersants, suspended powders and other substances which affect rheological behaviour and consequently the stability and application of the cosmetic composition.

They may be of natural or synthetic, mineral or organic origin. Of the organic, those preferred are natural polymers such as alginates, carrageenans, agar agar, pectins, starches, cellulose and their chemically modified derivatives; synthetic polymers such as acrylic polymers, which may or may not be hydrophobically modified, hydrophobically modified urethanes, alkene/styrene copolymers, polyethylene, polyamides, polyesters, polyethylene glycol derivatives, ethoxylated fatty alcohols, fatty acids and their salts. Examples of inorganic rheological modifiers are clays, silicas and their modified derivatives, magnesium and/or aluminium silicates.

A class of rheological modifiers which is particularly suitable for use in the lipophilic compositions according to this invention comprises suspended powders.

The lipophilic cosmetic compositions containing diglycerol tetrapelargonate according to the embodiments of the invention illustrated hitherto have good flow properties and luminosity. As a result of their light and delicate feel they are therefore suitable for example for the preparation of products for care of the body and hair, or make-up products, as a result of the glossy and brilliant effect imparted by diglycerol tetrapelargonate.

The cosmetic compositions according to the invention containing diglycerol tetrapelargonate in a mixture with other esters of pelargonic acid have different characteristics depending upon their composition.

For example, binary mixtures of diglycerol tetrapelargonate with neopentyl glycol dipelargonate and/or glycerol tripelargonate form a thin velvety film and impart a brilliant and luminous finish to the lipophilic cosmetic compositions containing them.

Binary mixtures of diglycerol tetrapelargonate and pentaerythritol tetrapelargonate form a rich substantial film and impart a shiny and bright effect to lipophilic cosmetic compositions.

Ternary mixtures of diglycerol tetrapelargonate with at least two esters selected from pentaerythritol tetrapelargonate, glycerol tripelargonate and neopentyl glycol dipelargonate form a thin film and impart a brilliant and luminous effect and optimum flow properties on the lipophilic cosmetic compositions containing them.

Quaternary mixtures of diglycerol tetrapelargonate with pentaerythritol tetrapelargonate, glycerol tripelargonate and neopentyl glycol dipelargonate form a substantial film in addition to imparting a brilliant and luminous effect and optimum flow properties on the lipophilic cosmetic compositions containing them.

Thanks to their good ability for dispersing UVA/UVB sun filters the compositions according to the invention are particularly suitable for application in sun protection products; compositions comprising mixtures of diglycerol tetrapelargonate and pentaerythritol tetrapelargonate are particularly suited for the purpose.

In accordance with another aspect, the invention relates to powder-based lipophilic compositions, that is compositions predominantly comprising one or more powder components selected from talc, mica, kaolin, silica, starches, silica-coated mica and talc, titania, titania-coated mica and talc, starches, apatite, perlite, polymers such as for example nylon and polyethylene, copolymer microspheres, silicone resin microbeads, or their mixtures. They advantageously comprise more than 35% by weight, preferably more than 40% by weight and more preferably more than 50% by weight of powder component. The said powder-based compositions comprise a binding component which in turn comprises or advantageously consists of diglycerol tetrapelargonate. The compositions according to this aspect advantageously also comprise texturising agents, colouring agents and possibly perfume and a preservative system.

These compositions find application in products such as eye shadow, blushers, face powders, earths and loose and compact powders. The said powder-based compositions advantageously comprise from 0.1% to 20% by weight, more preferably from 0.1% to 15% by weight, of the said binding component with respect to the weight of the cosmetic composition. In particular the said binding component preferably comprises from 1 to 10% by weight of compositions in the form of compact powders and from 1 to 5% by weight in compositions in the form of loose powders.

The preparation of powder-based compositions containing diglycerol tetrapelargonate preferably requires the addition of other binding agents to achieve a degree of adhesion between the components and spreadability which makes them acceptable for the final user. With regard to the binding component, diglycerol tetrapelargonate is present in quantities of preferably 70% or less, more preferably 60% by weight or less.

Surprisingly, when the said ester is used in combination with an ester selected from neopentyl glycol dipelargonate, glycerol tripelargonate and pentaerythritol tetrapelargonate, this combination advantageously comprises a greater portion, for example up to 80%, of the binding component. Combinations of diglycerol tetrapelargonate with glycerol tripelargonate and pentaerythritol tetrapelargonate are preferred.

The powder-based cosmetic compositions according to the invention have good compactness and spreadability. Due to their peculiar sensorial and functional properties, small amounts of the ester of pelargonic acid of the present invention are in fact advantageously required to bind talc when compared to the amount of vegetable oil typically required as binder in powder-based cosmetic compositions, with greater covering power when pentaerythritol tetrapelargonate is also present.

The said powder-based compositions may optionally comprise other ingredients of the oily or waxy type among the binding agents, in addition to the mixtures according to the invention. The oils previously listed as being typical ingredients of the oily component of anhydrous compositions and all the waxes typically used in cosmetic compositions for example have a binding action.

Examples of binding agents which may advantageously be added to powder-based compositions together with the mixtures of esters according to the invention are hydrocarbons such as polydecene, esters such as octyldodecyl stearyl stearate, triglycerides such as the triglyceride of capric/caprylic acids, fluid silicones, and lanolin derivatives.

Salts of fatty acids such as magnesium stearate, zinc stearate, calcium stearate, lithium stearate, aluminium stearate and their mixtures are also advantageously used in combination with the mixtures of esters according to the invention in the said powder-based compositions.

In accordance with a preferred embodiment the invention relates to a powder-based cosmetic composition in anhydrous form comprising, with respect to the weight of the cosmetic composition:
(a) from 35 to 99% by weight of powder,
(b) from 1 to 20% by weight, preferably from 3 to 15% by weight, of a binding component comprising diglycerol tetrapelargonate, optionally mixed with at least one ester selected from neopentyl glycol dipelargonate, glycerol tripelargonate and pentaerythritol tetrapelargonate,
(c) from 0 to 30% by weight of one or more texturising agents,
(d) from 0 to 15% by weight, preferably from 2 to 10%, of one or more colouring agents,
(e) from 0 to 15% by weight, preferably from 1 to 15%, more preferably from 5 to 15% by weight of a salt of a fatty acid,
(f) from 0 to 2% by weight, preferably from 0.01 to 1%, of one or more preservatives.

Binding components (b) comprising binary mixtures of diglycerol tetrapelargonate with one of the aforesaid esters of pelargonic acid are preferred.

Examples of texturising agents advantageously used in the said compositions are starches, starches modified with hydrophobic groups, polymers such as polyamides, polyurethanes and polyacrylates, in particular polymethyl methacrylates.

The cosmetic compositions in lipophilic form according to this invention preferably contain water in a quantity not exceeding 20%; preferably the water content is less than 10%, more preferably less than 8% and even more preferably less than 5% with respect to the weight of the cosmetic composition.

Aqueous Cosmetic Compositions (ii)

Diglycerol tetrapelargonate is also particularly suitable as an ingredient for aqueous cosmetic compositions, for example in the form of oil-based or water-based emulsions, in the form of microemulsions or hydrolipid dispersions, or in two-phase form.

The cosmetic compositions in aqueous form according to the invention preferably comprise more than 20%, preferably more than 35% and even more preferably more than 50% by weight of a hydrophilic or aqueous component comprising water. Together with the aqueous component these also contain a lipophilic component which in turn comprises or advantageously consists of diglycerol tetrapelargonate. According to a preferred aspect the said lipophilic component also comprises one or more esters selected from neopentyl glycol dipelargonate, glycerol tripelargonate and pentaerythritol tetrapelargonate.

The said cosmetic compositions in the aqueous form advantageously comprise from 0.1% to 50% by weight, more preferably from 0.1% to 35% by weight with respect to their weight of the said lipophilic component, of which diglycerol tetrapelargonate advantageously comprises up to 90%.

In addition to the abovementioned esters of pelargonic acid, the said lipophilic component may comprise other components in liquid form at ambient temperature (25° C.) and atmospheric pressure, such as oils of vegetable, animal, mineral and/or synthetic origin, preferably selected from esters, amides, ethers, alcohols and hydrocarbons of natural and/or synthetic origin, silicone oils or mixtures thereof. Typical examples are the oils listed above as being typical ingredients of the oily component of lipophilic compositions.

In accordance with a preferred aspect of the invention the aqueous cosmetic compositions may be in the form of oil-based emulsions (water in oil, A/O), or water-based emulsion (oil in water, O/A) or in the form of multiple emulsions (for example A/O/A or O/A/O).

In the case of the emulsions the lipophilic component may comprise, in addition to the mixtures according to the invention, other components in solid or pasty form at ambient temperature (25° C.) and atmospheric pressure, such as butters and/or waxes. Examples of butters are karite butter, cocoa butter, cupuacu butter. Suitable waxes are all the waxes commonly used in cosmetic compositions.

The cosmetic compositions in the form of oil-based emulsions according to the invention advantageously comprise up to 50% by weight, preferably up to 35%, more preferably up to 25% by weight of diglycerol tetrapelargonate with respect to the weight of the cosmetic composition. In addition to this the lipophilic component of the said oil-based emulsions advantageously comprises at least one oil from those listed above, for example a silicone oil. A preferred example of oil-based emulsions according to this invention are silicone-based emulsions (A/Si) in which the lipophilic component comprises one or more silicone oils and diglycerol tetrapelargonate.

In the lipophilic-based emulsions according to the invention diglycerol tetrapelargonate advantageously comprises up to 80% by weight of the lipophilic component. In the case where it is present in the form of a binary mixture with neopentyl glycol dipelargonate, the said mixture may advantageously comprise up to 70% by weight of the said lipophilic component, while its binary mixtures with glycerol tripelargonate or pentaerythritol tetrapelargonate advantageously constitute up to 60% by weight thereof. According to a preferred aspect of the invention in which the cosmetic compositions contain ternary mixtures of diglycerol tetrapelargonate, neopentyl glycol dipelargonate and glycerol tripelargonate and quaternary mixtures of diglycerol tetrapelargonate, neopentyl glycol dipelargonate, glycerol tripelargonate and pentaerythritol tetrapelargonate, the said mixtures may be used as the sole ingredient of the lipophilic component.

According to a preferred embodiment the invention relates to an aqueous cosmetic composition in the form of an oil-based emulsion comprising, with respect to the weight of the cosmetic composition:

(a) from 35 to 80% by weight of an aqueous phase;
(b) from 10% to 50% by weight, preferably from 10 to 35% of a lipophilic component comprising diglycerol tetrapelargonate, optionally in a mixture with at least one ester selected from neopentyl glycol dipelargonate, glycerol tripelargonate and pentaerythritol tetrapelargonate;
(c) from 0.3% to 15% by weight of one or more emulsifiers with an HLB of preferably between 3 and 6.

Typically the said aqueous phase comprises from 60 to 80% by weight and the said lipophilic component comprises 25-35% by weight of the cosmetic composition.

The said aqueous phase may contain chelating agents, such as for example ethylenediamine tetraacetic acid and its sodium salts (e.g. disodium, trisodium and tetrasodium salts), sodium chloride, magnesium sulfate and other stabilisers, preservatives, active ingredients and hydrating agents.

The compositions in the form of an oil-based emulsion according to this embodiment are suitable for example for the preparation of creams, sun creams, sera, foundation creams, concealers and mascara.

The cosmetic compositions in the form of water-based emulsion according to the invention advantageously comprise up to 40%, preferably up to 20%, even more preferably up to 15% by weight of a lipophilic component comprising diglycerol tetrapelargonate.

In the water-based emulsions according to the invention the diglycerol tetrapelargonate advantageously comprises up to 90% of the lipophilic component. In aqueous cosmetic compositions comprising diglycerol tetrapelargonate in a mixture with neopentyl glycol dipelargonate the said mixtures may advantageously comprise up to 80% by weight of the lipophilic component.

Binary mixtures of diglycerol tetrapelargonate with glycerol tripelargonate or pentaerythritol tetrapelargonate may advantageously comprise up to 70% or 60% by weight of the lipophilic component respectively.

Ternary mixtures of diglycerol tetrapelargonate with neopentyl glycol dipelargonate and glycerol tripelargonate, which may constitute up to 50%, preferably up to 10%, more preferably up to 5% by weight with respect to the weight of the said cosmetic compositions in the form of water-based emulsion are also advantageously used and are preferably used together with other oils, butters or waxes.

According to a preferred embodiment the invention relates to an aqueous cosmetic composition in the form of a water-based emulsion comprising, with respect to the weight of the cosmetic composition:
(a) from 60 to 90% by weight of an aqueous phase;
(b) from 0.5% to 40% by weight, preferably from 1 to 20%, of a lipophilic component comprising diglycerol tetrapelargonate, optionally mixed with at least one ester selected from neopentyl glycol dipelargonate, glycerol tripelargonate and pentaerythritol tetrapelargonate;
(c) from 5% to 15% by weight of one or more emulsifiers with an HLB of preferably between 6 and 12.

The compositions in the form of water-based emulsion, according to this embodiment, are for example suitable for the preparation of creams, milks, serums, butters, sun protection products, hair products such as balms, masks, leave-ons and make-up products, such as foundation creams, mascaras, concealers, and products for making up the lips.

Typical emulsifying agents used in compositions according to the invention have long or medium-length alkyl chains (generally longer than C12), and may be anionic, cationic, amphoteric or non-ionic.

The said emulsifying agents may be selected for example from the group comprising monoglycerides of fatty acids, sorbitan esters (for example monoesters, diesters, triesters and their mixtures) which may optionally be ethoxylated, saccharose esters, protein condensates with fatty acids, polyglycerols and/or their esters with fatty acids, ethers of glucose and/or polyglucose with fatty alcohols, lecithin and/or hydrogenated lecithin, ethoxylated fatty alcohols, ethoxylated fatty acids (for example PEG-100 stearate), soaps such as triethanolamine stearate, ethoxylated and non-ethoxylated phosphoric esters (for example potassium cetyl phosphate).

Emulsifying agents suitable for oil-based emulsions typically have unsaturated, branched or substituted alkyl chains, such as for example the oleic, isostearyl, ricinoleic and hydroxystearyl chains.

Emulsifying agents suitable for water-based emulsions typically have saturated and linear chains, such as for example stearyl and palmitoleic chains.

In accordance with another aspect, the cosmetic compositions in the form of water-based emulsion according to the invention advantageously comprise up to 15%, preferably up to 10% and more preferably up to 5% by weight of diglycerol tetrapelargonate.

According to a particularly preferred aspect the invention relates to aqueous cosmetic compositions comprising, with respect to the total weight of the cosmetic composition:
(a) from 60 to 90% by weight of an aqueous component;
(b) from 0.5% to 15% by weight, preferably from 1 to 10%, of a lipophilic component comprising diglycerol tetrapelargonate, optionally mixed with at least one ester selected from neopentyl glycol dipelargonate, glycerol tripelargonate and pentaerythritol tetrapelargonate;
(c) from 8% to 40% by weight of one or more surfactants.

Among these compositions, those preferred are those in which the diglycerol tetrapelargonate or mixture thereof with neopentyl glycol dipelargonate constitutes up to 12%, preferably from 0.1% to 10%, with respect to the weight of the lipophilic component. Also preferred are compositions in which the lipophilic component also comprises vegetable oils in addition to the abovementioned ester or mixture of esters.

In such aqueous cosmetic compositions the said surfactants have the function of reducing surface tension, encouraging detergency; they may or may not have a foam-generating function and may be non-ionic, anionic, amphoteric or cationic.

Typical surfactants used in compositions according to the invention typically have short or medium-length alkyl chains (generally shorter than C14), such as for example those of capric, caprylic and lauric acids.

They may be selected for example from the group comprising: alkyl sulfates and/or alkyl ether sulfates, preferably of Na, Mg, Zn or ammonium (NH4), monoethanolamine (MEA), triethanolamine (TEA) or monoisopropylamine (MIPA); alkyl ether carboxylates; protein condensates with fatty acids; acyl glutamates; acyl sarcosinates; acyl isothionates; acyl methyl taurates; alkyl sulfosuccinates; soaps; alkyl betaine and alkylamidopropyl betaine; alkyl and alkylamidohydroxy sultaine; alkyl amphoacetates and alkyl amphodiacetates; alkyl amphopropionates and alkyl amphodipropionates; alkyl and alkylamidopropyl aminoxides; polysorbates (e.g. polysorbate 20); monosaccharose esters; alkyl glucosides; quaternary ammonium salts.

Those skilled in the art will readily be able to determine the quantity of surfactant required on the basis of the type of cosmetic product for which the composition is intended. For example, cosmetic compositions intended for the preparation of intimate detergents typically contain a quantity of surfactants comprising from 8 to 10% by weight; shampoos from 10 to 15% by weight; shower foam from 13 to 18% by weight, and bath foam from 18 to 22% by weight. The compositions in the form of a single phase aqueous solution according to this aspect of the invention may advantageously take the form of microemulsions; they are suitable for example for the preparation of bath foam, shower gel, detergents, shampoos, liquid soaps, and therefore "rinse-off" products but also "leave-on" products.

According to another preferred aspect of the invention the said aqueous cosmetic compositions are in two-phase form, that is they have an aqueous phase which is separate from the lipophilic phase in two separate layers. Cosmetic products prepared with these compositions typically require mixing before use, which results in the formation of temporary emulsions.

Preferably the said compositions comprise, with respect to the total weight of the cosmetic composition:
(a) from 50 to 70% by weight of an aqueous phase;
(b) from 30% to 50% of a lipophilic phase comprising diglycerol tetrapelargonate, optionally mixed with at least one ester selected from neopentyl glycol dipelargonate, glycerol tripelargonate and pentaerythritol tetrapelargonate.

The said compositions in two-phase form preferably comprise up to 50% by weight, more preferably between 0.1 and 30% by weight, even more preferably between 0.1 and 10% by weight, of diglycerol tetrapelargonate with respect to the weight of the lipophilic phase. Compositions in which the lipophilic phase comprises diglycerol tetrapelargonate or a mixture thereof with neopentyl glycol dipelargonate in quantities advantageously up to 30% by weight with respect to the weight of the lipophilic phase are preferred.

In addition to the abovementioned esters of pelargonic acid, the lipophilic phase preferably comprises mineral and/or silicone oils, for example isododecanes, cyclopentasiloxane, reaction products between propylene oxide and stearyl alcohols (such as polypropylene glycol-15-stearyl ether), vegetable oils such as almond, olive or jojoba oils.

The aqueous compositions in two-phase form according to this aspect of the invention are suitable for example for the preparation of make-up removers.

The cosmetic compositions according to the invention, whether in the form of an anhydrous composition or an aqueous composition, may comprise one or more sun filters, as described above, in the case of anhydrous compositions. The said sun filters are used in quantities of preferably between 0.05% and 35% by weight, preferably between 0.1 and 25%, with respect to the weight of the cosmetic composition.

Thanks to the properties of the pelargonic acid esters present in them, the compositions according to the invention have the particular advantage that they ensure optimum dispersion and/or dissolution of sun filters, whose stability may increase when used in an emulsion, and whose protection factor they may help to increase. They are therefore suitable for use in cosmetic compositions intended for protection from the sun, care of the body and hair, and make-up products having a protective and anti-aging action.

Compositions comprising diglycerol tetrapelargonate in a mixture with pentaerythritol tetrapelargonate and/or glycerol tripelargonate, whose flow and viscosity properties are particularly marked and which are provided with particular emollience, are particularly suitable for this purpose. Mixtures comprising pentaerythritol tetrapelargonate are more preferred.

The cosmetic compositions according to the invention may also comprise one or more colouring agents or dyes, in quantities of preferably between 0.1% and 35% by weight, more preferably between 0.1 and 30% by weight, even more preferably between 0.1 and 20% by weight.

The said colouring agents may be soluble or insoluble in water, soluble or insoluble in fats, mineral or organic, natural or synthetic, and have the function of colouring or opacifying the cosmetic composition. Examples of suitable colouring agents are pigments, lacquers or pearls, which may be used as such or after surface treatments intended for example to modify water-repellence or hydrophilic properties. The pigments include derivatives of metals of an inorganic nature, for example oxides of iron, cerium, chromium, titanium, zinc or zirconium, silicates (e.g. micas), sulfosilicates (e.g. ultramarine) and their combinations, and molecules of an organic nature, such as for example plant extracts. By the term "pearls" are meant special pigments capable of developing reflection and refraction phenomena with light, which may be iridescent or non-iridescent, either organic (such as guanine, CI 75170) or inorganic (such as bismuth oxychloride, CI 77163, or sericite, CI 77019).

Surprisingly, diglycerol tetrapelargonate has shown a higher solubilisation and dispersion rate of pigments when compared to some of the commonly used oily solvents/dispersants and even when compared to structurally similar tetraesters of pelargonic acid, such as pentaerythritol tetrapelargonate. Mixtures of diglycerol tetrapelargonate with the aforesaid pelargonic acid esters have the particular advantage to further assist the dispersion of pigments. As a result, they may contribute to intensifying their colour.

The cosmetic compositions according to the invention may also comprise one or more additives selected from those typically used in cosmetic compositions such as for example antioxidants and/or vitamins, preservatives, pH modifiers, humectants (such as for example glycerine, sorbitol, glycols, polyethylene glycols), conditioners, chelating agents, rheological modifiers, texturising agents, film-forming agents, silicones, perfumes, essential oils, and active ingredients, in particular cosmetic and/or dermatologically active ingredients. Each additive may be present in a quantity from 0 to 35%, preferably from 0 to 20% by weight, more preferably from 0 to 10% with respect to the total weight of the cosmetic composition.

By the term "preservatives" according to the invention are meant natural or synthetic substances having the primary function of inhibiting the growth of microorganisms in the cosmetic composition. The list of permitted preservatives makes reference to Appendix V to EC Regulation 1223/2009. The maximum permitted percentages used, any limitations and methods of use may be found within the document. The most widely used preservatives include for example: benzoic acid, propionic acid, salicylic acid, sorbic acid and their salts, p-hydroxybenzoic acid, its salts and esters, dehydroacetic acid, potassium sorbate, phenoxyethanol, imidazolidinyl urea. In combination or as an alternative to the said preservatives the cosmetic compositions according to the invention may also contain other substances capable of contributing to inhibition of the growth of microorganisms such as for example honey, essential oils such as extracts of rosemary, *Melaleuca alternifolia* and thyme, and complexing agents such as EDTA.

The cosmetic compositions according to the invention may be prepared according to processes known to those skilled in the art in the cosmetics industry.

For example, a preferred method of preparing lipophilic cosmetic compositions according to the invention comprises mixing the ingredients of the cosmetic composition, advantageously after any solid components have been brought to their melting points, using specific equipment, such as for example a three-roll refiner, which results in a fine dispersion of any additives.

A preferred manner of preparing the powder-based lipophilic cosmetic compositions according to the invention comprises one or more cycles of grinding the powders (including pigments and texturising agents) in suitable mills, preferably provided with cooling systems to ensure that the heat produced during grinding is dispersed; the length of the mixing and grinding cycles can be readily identified by those skilled in the art on the basis of the nature of the powders. Once the size and degree of uniformity required for the powders has been achieved, the binding component is gradually added to the powders, preferably after its ingredients have been mixed and they, including liposoluble preservatives, have been raised to melting point or a temperature above that (typically 5-10° C. above the melting point), when ingredients in solid or semi-solid form such as waxes and hydrogenated derivatives are present. The mixture so obtained then undergoes further mixing cycles to encourage incorporation of the binding component, with any pearlescent pigments being added at this stage. Subsequently the desired quantity of composition preferably undergoes one or more operations selected from grinding, sieving or pressing in a mould.

One manner of preparing aqueous cosmetic compositions according to the invention instead, for example, comprises subjecting the desired quantity of ingredients to mixing by means of mixers and/or turboemulsifiers of suitable capacity, preferably provided with heat-regulating systems so as to operate at suitable temperatures depending upon the stability and melting points of the ingredients.

The cosmetic compositions according to this invention may take solid, pasty or liquid form. Diglycerol tetrapelargonate and its mixtures with one or more esters selected from neopentyl glycol dipelargonate, glycerol tripelargonate and pentaerythritol tetrapelargonate therefore find application in coloured or non-coloured cosmetic compositions for care, make-up, protection from the sun and cleansing of the skin and cutaneous annexes.

They may advantageously be used for the preparation of creams, milks, sun creams, sera, butters, foam bath, shower gel, detergents, shampoos, leave-on products, balsams, masks and leave-ons for the hair, foundation creams, mascara, lipstick, eye shadow, blushers and compact powders.

EXAMPLES

The esters used in the following examples were prepared by using pelargonic acid obtained from the oxidative cleavage of sunflower oil having a high oleic acid content. In particular the pelargonic acid was obtained according to the process described in patent application WO 2011080296, at the end of stage c) of separating the monocarboxylic acids from the triglycerides containing more than one acid functional group and after a subsequent rectification stage to remove the fraction comprising light monocarboxylic acids, as described in Example 1. The pelargonic acid used had a purity of 99%. The diglycerol tetrapelargonate used has a purity of 92.6%, with a glycerol content of 1.7%, triglycerol of 5.4% and 0.3% by weight of higher polyglycerols.

Preparation of Diglycerol Tetrapelargonate

The esterification reactions for synthesis of the ester were carried out in the absence of catalyst and with a molar excess of pelargonic acid equal to 30% molar with respect to the diglycerol used. In order to encourage removal of the water of esterification, in the course of the reactions the temperature of the acid/polyol mixture was increased up to 200-210° C.; once this temperature had been reached, gradual vacuum was applied up to 100 mbar, so as to encourage conversion of the reagents. On completion of the reaction, after a quantity of water of reaction corresponding to the theoretical had been collected, the excess acid was recovered by evaporation by holding the temperature around 180-200° C. and applying a vacuum of between 5 and 10 mbar.

The product then underwent bleaching treatment with activated carbon and decolouring earth and neutralisation through the addition of a quantity of calcium hydroxide and water (in a ratio of 1:1 by weight) comprising between 1 and 2% by weight with respect to the ester, heating with stirring at 60° C. for 30 minutes. After complete dewatering through heating at 80-100° C. under vacuum, the filtration earth (Celite 512; 1% by weight with respect to the ester) was added with stirring and was filtered off under vacuum on a bed of the same earth, yielding a clear product.

Acidity measurements, carried out in accordance with standard ASTM D664, revealed a residual acidity of less than 0.1 mg KOH/g.

Examples of cosmetic compositions according to the invention are shown in the following tables and compared to compositions containing known esters commonly used as cosmetic ingredients. The list of ingredients (according to the INCI nomenclature) and the percentage composition by weight of each ingredient with reference to the total weight of the composition are shown in the following tables.

Examples 1 (Comparison)-2: Moisturising Cream

Ingredients:

| | INCI | Example 1 (comparison) | Example 2 |
|---|---|---|---|
| A | Aqua | 75.4 | 75.4 |
| | Disodium EDTA | 0.1 | 0.1 |
| | Propylene Glycol | 1 | 1 |
| | Allantoin | 0.5 | 0.5 |
| | Chlorophenesin | 0.3 | 0.3 |
| B | Carbomer | 0.5 | 0.5 |
| C | Ceteareth-30 | 5 | 5 |
| | Arachydyl Alcohol, Behenyl Alcohol, Arachydyl Glucoside | 4 | 4 |
| | Argania Spinosa Kernel Oil, Palmitic/Stearic Triglyceride | 3 | 3 |
| | Ethylhexyl Stearate | 7 | — |
| | Diglyceryl Tetrapelargonate | — | 7 |
| | Tocopheryl Acetate | 0.1 | 0.1 |
| | O-cymen-5-ol | 0.1 | 0.1 |
| D | Water | 1.5 | 1.5 |
| | Triethanolamine | 0.5 | 0.5 |
| E | Perfume | 0.2 | 0.2 |
| F | Aloe Barbadensis Leaf Juice | 0.8 | 0.8 |

Preparation:

The ingredients in group A were weighed and mixed in a gently stirred turboemulsifier, heating to a temperature of 70±2° C.

Ingredient B was weighed separately, then added to mixture A, stirring at constant speed until it was completely dissolved.

The ingredients in group C were weighed in the fat melter, heating to 70±2° C. with constant stirring.

When both the mixtures had reached 70±2° C., mixture C was drawn by vacuum into the turboemulsifier containing mixture A+B, with gentle stirring. After mixture C had been transferred to the turboemulsifier, stirring was continued under vacuum until emulsification was complete.

The emulsion was then cooled, again with stirring, to a temperature of 40±2° C.

The ingredients of group D (prepared separately) were added at this temperature, drawing them over under vacuum and keeping them stirred until a homogeneous mixture was obtained.

Ingredients E and F were then added, maintaining stirring for approximately 10 minutes after each addition to ensure uniform mixing. Once the specifications had been achieved the product was cooled to ambient temperature (with stirring) and discharged into suitably provided containers.

The compositions obtained had a pH of 5.5-6.5 and passed the 1 month stability tests at 4° C., 40° C., 25° C. and in the light.

The aqueous cosmetic composition according to the invention (Example 2), in which the lipophilic component contains diglycerol tetrapelargonate (7% by weight in relation to the total for the composition) demonstrated the same properties as a comparison composition (Example 1) in which the same quantity of lipophilic component comprised ethylhexyl stearate.

Examples 3 (Comparison)-4: Conditioning Cream for the Hair

Ingredients:

| | INCI | Example 3 (comparison) | Example 4 |
|---|---|---|---|
| A | Aqua | 77.1 | 77.1 |
| | Butylene Glycol | 2 | 2 |
| | Disodium EDTA | 0.1 | 0.1 |
| | Panthenol | 0.5 | 0.5 |
| | Chlorphenesin | 0.3 | 0.3 |
| B | Sericin | 0.2 | 0.2 |
| C | Cetrimonium Chloride | 6 | 6 |
| | Cetearyl Alcohol | 6 | 6 |
| | C12-13 Alkyl Lactate | 6 | — |
| | Diglyceryl Tetrapelargonate | — | 6 |
| | Olive Glycerides, Ceramide NP | 0.5 | 0.5 |
| | O-Cymen-5-ol | 0.1 | 0.1 |
| | Tocopheryl Acetate | 1 | 1 |

Preparation:

The ingredients in group A were weighed and mixed in a constantly stirred turboemulsifier, heating to 70±2° C.; ingredient B was weighed and then added to mixture A, continuing stiffing for a sufficient time to ensure uniform mixing. The ingredients of group C were weighed in the fat melter, heating to 70±2° C. with constant stirring. When both the mixtures reached 70±2° C. mixture C was drawn over by vacuum into the turboemulsifier containing mixture A+B, with gentle stirring. When transfer to the turboemulsifier was complete, stiffing was continued under vacuum until emulsification was complete.

Again under vacuum and with constant stirring the system was then cooled to 40±2° C. Once the specifications for the product had been checked it was cooled to ambient temperature (under vacuum and with constant stirring) and discharged into suitably provided containers. Both the compositions obtained were in the form of a white emulsion, with a pH of between 4.5 and 5, and demonstrated the same performance. They also passed the stability tests, with their organoleptic and pH characteristics remaining unchanged after 1 month at 4° C., 40° C. and 25° C. and in the light.

Examples 5 (Comparison)-6: Lipstick

Ingredients:

| | INCI | Example 5 (comparison) | Example 6 |
|---|---|---|---|
| A | Octyldodecanol | 17.19 | 17.19 |
| | Candelilla Wax | 10.00 | 10.00 |
| | Copernicia Cerifera Wax | 1.76 | 1.76 |
| | Cera Alba | 8.82 | 8.82 |
| | Caprylic, Capric Triglyceride | 6.12 | 6.12 |
| | Diisostearyl Malate | 10.50 | — |
| | Diglyceril Tetrapelargonate | — | 10.50 |
| | Pentaerythrityl Tetraisostearate | 30.40 | 30.40 |
| | Polyglyceryl-2 Isostearate/ Dimer Dilinoleate Copolymer | 4.71 | 4.71 |
| | Tocopheryl Acetate | 0.50 | 0.50 |
| B | Synthetic Wax, Red 7 Lake, Isopropyl Titanium Triisostearate | 5.80 | 5.80 |
| | Synthetic Wax, Titanium Dioxide, Isopropyl Titanium Triisostearate | 4.20 | 4.20 |

Preparation:

The ingredients in group A were placed in a mixer and heated to a temperature of 90° C. When they reached that temperature the ingredients in stage B were added with stiffing, mixing until the mixture was completely homogenised, continuing to heat to hold the temperature at around 80° C. The mixture so obtained was then poured into moulds and allowed to cool.

The lipophilic cosmetic composition according to the invention (Example 6) whose lipophilic component contains diglycerol tetrapelargonate (10.5% by weight in relation to the total for the composition) demonstrated the same properties as a comparison composition (Example 5) in which the same quantity of lipophilic component comprised diisostearyl malate, albeit their difference in the chemical structure.

Examples 7-8 (Comparison) and 9: Hydrating Cream

Ingredients:

| | INCI | Example 7 (comparison) | Example 8 (comparison) | Example 9 |
|---|---|---|---|---|
| A | Aqua | 75.40 | 75.40 | 75.40 |
| | Disodium EDTA | 0.10 | 0.10 | 0.10 |
| | Propylene Glycol | 1.00 | 1.00 | 1.00 |
| | Allantoin | 0.50 | 0.50 | 0.50 |
| | Chlorphenesin | 0.30 | 0.30 | 0.30 |
| B | Carbomer | 0.50 | 0.50 | 0.50 |
| C | Ceteareth-30 | 5.00 | 5.00 | 5.00 |
| | Arachhydyl Alcohol, Behenyl Alcohol, Arachydyl Glucoside | 4.00 | 4.00 | 4.00 |
| | Argania Spinosa Kernel Oil, C10-C18 Triglycerides | 3.0 | 3.0 | 3.0 |
| | Ethyl hexyl stearate | 7.00 | — | — |
| | Pentaerythritol tetrapelargonate | — | 7.00 | — |
| | Diglycerol tetrapelargonate | — | — | 7.00 |
| | O-Cymen-5-Ol | 0.10 | 0.10 | 0.10 |
| | Tocopheryl Acetate | 0.10 | 0.10 | 0.10 |
| D | Aqua, | 1.50 | 1.50 | 1.50 |
| | Triethanolamine | 0.50 | 0.50 | 0.50 |
| E | Parfum | 0.20 | 0.20 | 0.20 |
| F | Aloe barbadensis Leaf Juice | 0.80 | 0.80 | 0.80 |

Ethyl hexyl stearate in comparative Example 7 was substituted by the same amount (7.00%) of pentaerythritol tetrapelargonate in comparative Ex. 8 and of diglycerol tetrapelargonate in Example 9.

Three water based emulsions were prepared according to the same procedure of Example 1 and subjected to a sensory evaluation. A panel of 20 female individuals was required to spread each composition on the back of the hand and provide a rating from 1 (low) to 3 (high) on the properties listed in the table below.

The composition comprising diglycerol tetrapelargonate showed higher softness, smoothness and absorption rate when compared both to ethyl hexyl stearate and to pentaerythritol tetrapelargonate. The composition comprising pentaerythritol tetrapelargonate showed the highest film-forming effect.

| Sensory evaluation | Example 7 (Ethyl hexyl stearate) | Example 8 (Pentaerythritol tetrapelargonate) | Example 9 (Diglycerol tetrapelargonate) |
|---|---|---|---|
| Softness | 2 | 2 | 3 |
| Smoothness | 1 | 1 | 2 |
| Greasiness | 3 | 3 | 2 |
| Stickiness | 3 | 3 | 1 |
| Film-forming effect | 2 | 3 | 2 |
| Absorption rate | 1 | 1 | 2 |

Example 10: Pigments Dispersion

Black Iron Oxide particles (CI77499, commercially available as YPC335200 from Yipin) were dispersed in diglycerol tetrapelargonate and in ester oils commonly used as cosmetic ingredients. Each sample of powder particles was wetted by the dropwise addition of one ester oil and then vigorously blended using a spatula until the wet point and the flow point were reached.

The wet point is defined as the minimum volume of dispersant solution to produce a soft coherent mass; the further minimum addition of dispersant solution to produce flow or falling off of the homogeneous mass from the vertical blade of a horizontally held spatula determines the flow point.

The amounts of dispersant solution (i.e. ester oil) needed to reach the wet point (Wp) and the flow point (Fp) were recorded and reported in the table below, expressed in grams per 100 g of pigment.

| Pigment dispersion | Wp (g) | Fp (g) |
|---|---|---|
| Isononyl Isononanoate | 50.00 | 145.00 |
| Caprylic/Capric Triglyceride | 60.00 | 130.00 |
| C12-15 Alkyl Benzoate | 60.00 | 143.00 |
| Pentaerythritol tetrapelargonate | 62.00 | 132.00 |
| Diglycerol tetrapelargonate | 55.00 | 100.00 |

Surprisingly, diglycerol tetrapelargonate has revealed a Fp significantly close to the Wp, demonstrating dispersion properties even better than those of Caprylic/Capric Triglyceride and of Pentaerythritol Tetrapelargonate. This minimum difference results in a considerable advantage as it enables significant cost savings on the final composition (wherein about 30% less solvent is required).

Examples 11 and 12-13 (Comparison) Lipstick

Three lipophilic cosmetic compositions were prepared in the form of lipsticks as described in Examples 5(comparison)-6, according to the following ingredients list:

| | INCI | Example 11 | Example 12 (comparison) | Example 13 (comparison) |
|---|---|---|---|---|
| A | Candelilla cera | 10.00 | 10.00 | 10.00 |
| | Copernicia Cerifera Cera | 1.76 | 1.76 | 1.76 |
| | Cera alba | 8.82 | 8.82 | 8.82 |
| | Octyldodecanol | 12.19 | 12.19 | 12.19 |
| | Diglycerol tetrapelargonate | 21.72 | — | — |
| | Pentaerythritol tetrapelargonate | — | 21.72 | — |
| | Diglycerol tetraoleate | — | — | 21.72 |
| | Polyglyceryl-2 Isostearate/ Dimer Dilinoleate Copolymer | 4.71 | 4.71 | 4.71 |
| | Pentaerythrityl Tetraisostearate | 30.30 | 30.30 | 30.30 |
| | Tocopheryl acetate | 0.50 | 0.50 | 0.50 |
| B | Synthetic wax, Red 7 Lake, Isopropyl Titanium triisostearate | 5.80 | 5.80 | 5.80 |
| | Synthetic wax, Titanium Dioxide, Isopropyl Titanium triisostearate | 4.20 | 4.20 | 4.20 |

Diglycerol tetrapelargonate in Example 11 was substituted by the same amount (21.72%) of pentaerythritol tetrapelargonate in comparative Ex. 12 and of diglycerol tetraoleate in comparative Example 13.

The three resulting compositions were subjected to a sensory evaluation. A panel of 20 individuals (women) was required to test the lipsticks and provide a rating from 1 to 5 on the properties listed in the table below.

Evaluation Scale:
5: Excellent
4: Very good
3: Good
2: Fair
1: Poor

| Sensory evaluation | Example 11 | Example 12 (comparison) | Example 13 (comparison) |
|---|---|---|---|
| Flowability | 5 | 3 | 3 |
| Fullness | 4 | 4 | 3 |
| Softness | 5 | 4 | 3 |
| Adherence | 4 | 4 | 4 |
| Uniformity of the film | 4 | 4 | 4 |
| Gloss effect | 4 | 4 | 4 |

The composition comprising diglycerol tetrapelargonate of Example 12 showed excellent flowability and softness, while fullness, adherence and homogeneity were comparable to those of the compositions of comparative Examples 13 and 14.

The invention claimed is:

1. A physiologically acceptable cosmetic composition in the form of a lipophilic composition or in the form of an aqueous composition comprising from 0.1% to 99% by weight of diglycerol tetrapelargonate, relative to the total weight of the cosmetic composition, said cosmetic composition being in solid, pasty or liquid form.

2. The cosmetic composition according to claim 1 further comprising one or more esters selected from neopentylglycol dipelargonate, glycerol tripelargonate, and pentaerythritol tetrapelargonate.

3. The cosmetic compositions according to claim 2 being in lipophilic form that comprises an oily component or in aqueous form.

4. The cosmetic composition according to claim 2 further comprising an oil selected from esters, ethers, amides, alcohols and hydrocarbons of natural and/or synthetic origin, silicone oils, or mixtures thereof.

5. The cosmetic compositions according to claim 1 being in lipophilic form that comprises an oily component or in aqueous form.

6. The cosmetic composition according to claim 5 being in lipophilic form that comprises an oily component and comprising up to 20% by weight of diglycerol tetrapelargonate, relative to the weight of the cosmetic composition.

7. The cosmetic composition according to claim 5, being in aqueous form comprising up to 50% by weight of diglycerol tetrapelargonate, relative to the weight of the cosmetic composition.

8. The cosmetic composition in aqueous form according to claim 7 comprising up to 15% by weight of diglycerol tetrapelargonate and comprising surfactants.

9. The cosmetic composition according to claim 1 further comprising an oil selected from esters, ethers, amides, alcohols and hydrocarbons of natural and/or synthetic origin, silicone oils, or mixtures thereof.

10. The cosmetic composition according to claim 1 further comprising one or more butters and/or one or more waxes.

11. The cosmetic composition according to claim 1 further comprising one or more oligomers.

12. The cosmetic composition according to claim 1 further comprising one or more sunscreens in quantities from 0.05% to 35% by weight.

13. The cosmetic composition according to claim 1 further comprising one or more dyes and/or one or more additives selected from antioxidants, vitamins, preservatives, pH modifiers, humectants, conditioners, chelating agents, rheology modifiers, texturizers, film-forming agents, silicones, perfumes, essential oils, and active components.

14. The cosmetic composition according to claim 13 wherein each of said dyes and/or additives is present in amounts from 0 to 35% by weight with respect to the total weight of the cosmetic composition.

15. The cosmetic composition according to claim 1 being a sun protection composition for protecting skin and/or skin appendages from the sun.

16. The cosmetic composition according to claim 1 for use in the care of the skin and hair, in make-up and in hygiene products.

17. A cosmetic composition comprising diglycerol tetrapelargonate, wherein the cosmetic composition is selected from the group of creams, milks, solar, serums, butters, bath foams, shower gels, detergents, shampoos, leave-on, balms, hair masks and leave-on, foundations, mascaras, lipsticks, lip glosses, concealers, eye shadows, blushers, face powders, loose powders and compact powders.

18. A method for the care, the make-up and/or for the cleansing of the skin and/or skin appendages which comprises applying a cosmetic composition according to claim 1 to said skin or skin appendage.

19. A mixture of diglycerol tetrapelargonate with one or more esters selected from neopentylglycol dipelargonate, glycerol tripelargonate, and pentaerythritol tetrapelargonate.

20. A cosmetic composition comprising the mixture according to claim 19, wherein the cosmetic composition is selected from the group of creams, milks, solar, serums, butters, bath foams, shower gels, detergents, shampoos, leave-on, balms, hair masks and leave-on, foundations, mascaras, lipsticks, lip glosses, concealers, eye shadows, blushers, face powders, loose powders and compact powders.

21. A method for the care, the make-up and/or for the cleansing of the skin and/or skin appendages which comprises applying a cosmetic composition according to claim 20 to said skin or skin appendage.

\* \* \* \* \*